United States Patent [19]

Takahashi

[11] Patent Number: 5,776,049

[45] Date of Patent: Jul. 7, 1998

[54] STEREO ENDOSCOPE AND STEREO ENDOSCOPE IMAGING APPARATUS

[75] Inventor: Susumu Takahashi, Iruma, Japan

[73] Assignee: Olympus Optical Co., Ltd., Tokyo, Japan

[21] Appl. No.: 449,269

[22] Filed: May 24, 1995

Related U.S. Application Data

[62] Division of Ser. No. 155,807, Nov. 23, 1993, Pat. No. 5,522,789.

[30] Foreign Application Priority Data

Dec. 24, 1992 [JP] Japan ............. 4-344814

[51] Int. Cl.$^6$ ............. A61B 1/00
[52] U.S. Cl. ............. 600/111; 600/166; 348/45; 350/473
[58] Field of Search ............. 600/111, 166; 348/42, 45, 46, 47, 49, 55–57; 359/462, 473; 354/112, 114

[56] References Cited

U.S. PATENT DOCUMENTS

| | | |
|---|---|---|
| 1,114,232 | 10/1914 | Cheron . |
| 3,520,587 | 7/1970 | Tasaki et al. . |
| 4,418,993 | 12/1983 | Lipton ............. 352/57 |
| 4,447,717 | 5/1984 | Nohda . |
| 4,469,415 | 9/1984 | Radl ............. 359/177 X |
| 4,573,191 | 2/1986 | Kidode et al. ............. 359/462 X |
| 4,862,873 | 9/1989 | Yajima et al. . |
| 4,924,853 | 5/1990 | Jones, Jr. et al. . |
| 4,926,257 | 5/1990 | Miyazaki . |
| 5,142,357 | 8/1992 | Lipton et al. ............. 348/47 |
| 5,193,000 | 3/1993 | Lipton et al. ............. 348/47 |
| 5,295,477 | 3/1994 | Janfaza ............. 600/166 X |
| 5,486,948 | 1/1996 | Imai et al. ............. 359/462 |

FOREIGN PATENT DOCUMENTS 1-161213   6/1989   Japan ............. 359/462

*Primary Examiner*—Richard J. Apley
*Assistant Examiner*—John Mulcahy
*Attorney, Agent, or Firm*—Armstrong, Westerman, Hattori, McLeland & Naughton

[57] ABSTRACT

A stereo endoscope including a pair of objective optical systems, a pair of relay optical systems, an imagery optical system having a single optical axis, and a pair of imaging devices. The imagery optical system is a zoom optical system or a varifocal optical system. For example, an encoder is used to detect a magnitude of moving lenses in the zoom optical system. Based on the detected magnitude, a control unit allows the two imaging devices to approach or depart from each other. Thus, the stereo endoscope attains the coincidence between observation points of right and left fields of view against the displacement points of right and left object images resulting from variations of zooming magnifications.

1 Claim, 16 Drawing Sheets

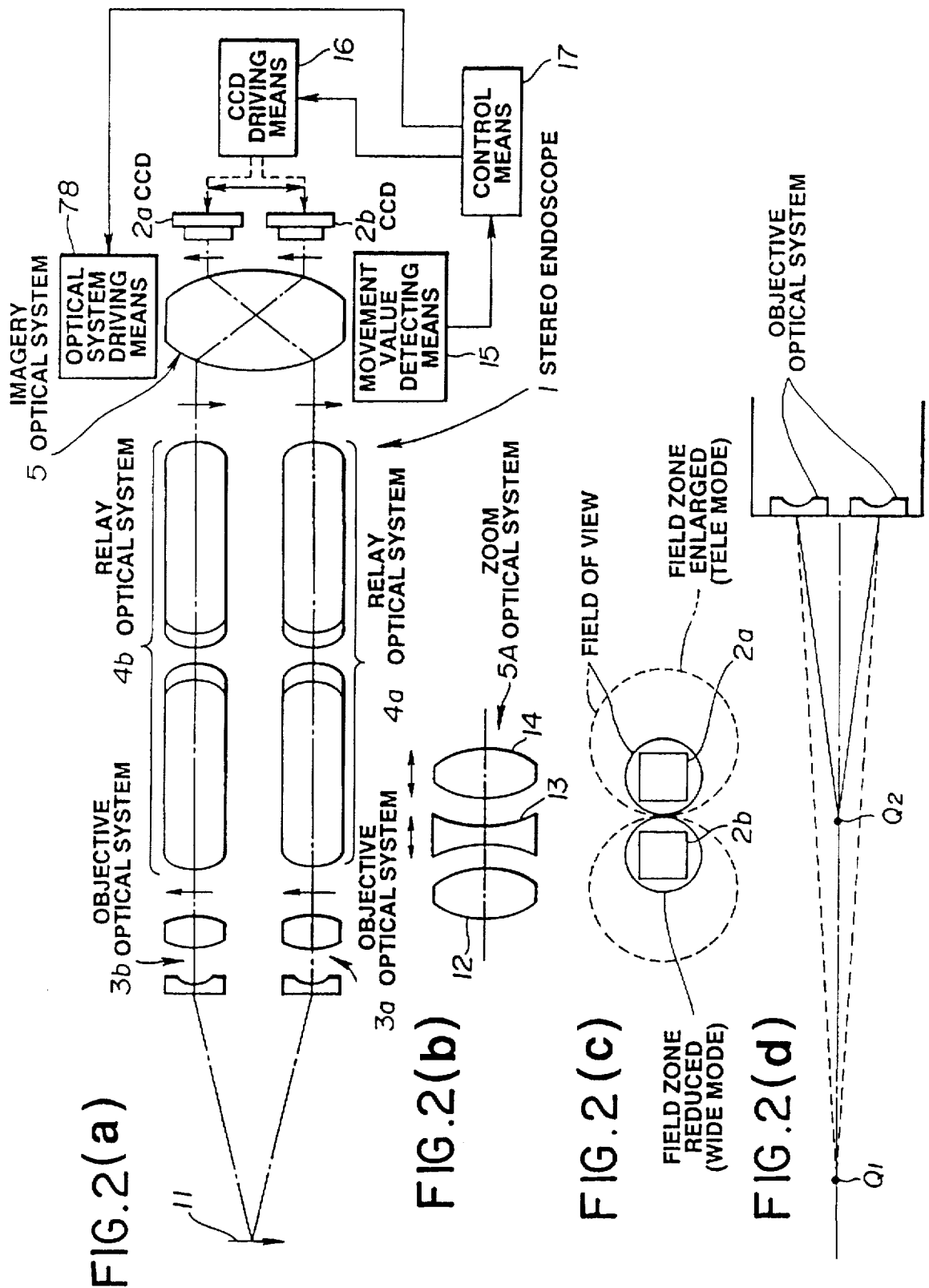

BEHIND THE RELAY SYSTEM

MAGNIFICATION SMALL

MAGNIFICATION LARGE

ON THE CCD

MAGNIFICATION LARGE

ON THE CCD

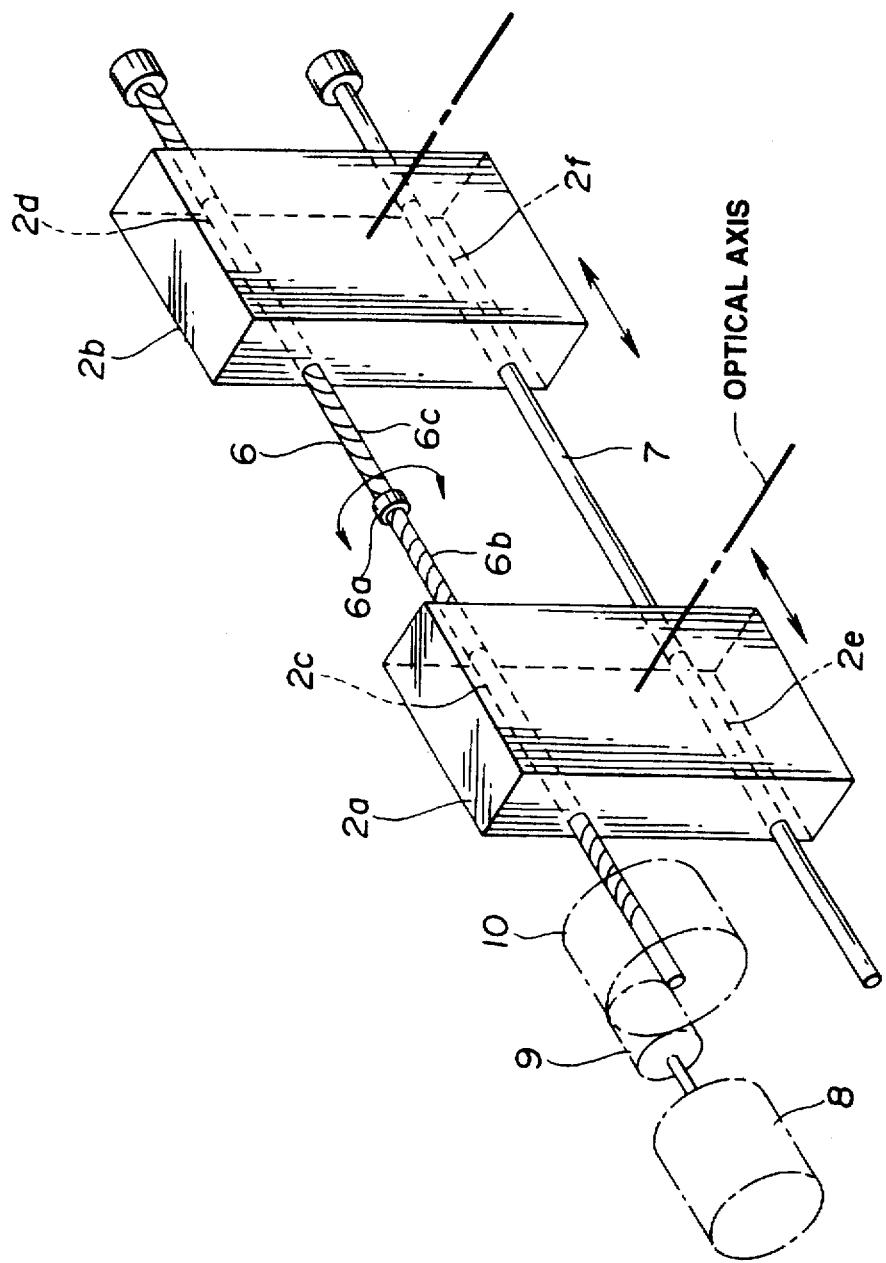

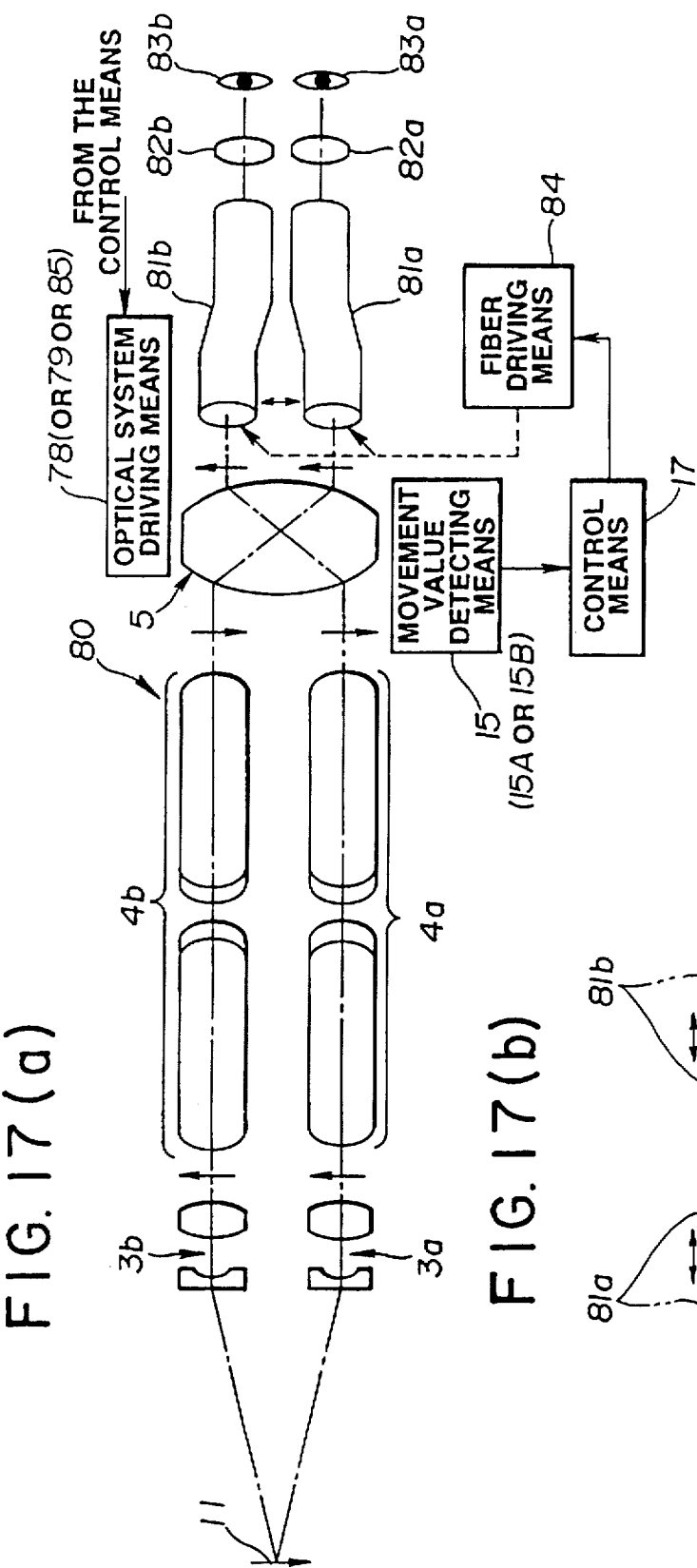
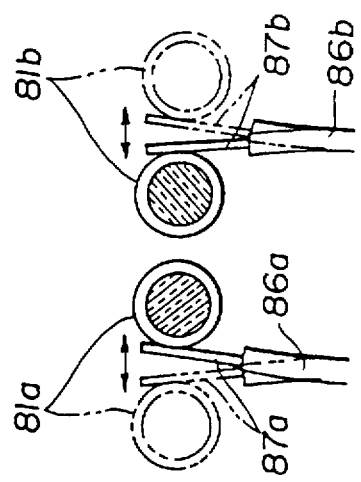
FIG. 17(a)
FIG. 17(b)

STEREO ENDOSCOPE AND STEREO ENDOSCOPE IMAGING APPARATUS

This is a division of application Ser. No. 08/155,807 filed Nov. 23, 1993, now U.S. Pat. No. 5,522,789.

BACKGROUND OF THE INVENTION

1. Field of the Invention

The present invention relates to a stereo endoscope and a stereo endoscope imaging apparatus which enable stereo observation of an object by producing a parallax.

2. Description of Related Art

Almost all endoscopes visualize an object to be examined, for example, the inside of a body cavity, as a plane without a depth. Conventional endoscopes have difficulties in visualizing the fine irregularities on the surface of an internal wall of a body cavity which are very important diagnostic indices. As a solution to this problem, a stereo endoscope has been proposed. For example, Japanese Patent Laid-Open No. 57-69839 has disclosed a stereo endoscope in which objective lenses are attached to one end of each of a pair of image guides, and eyepieces are attached to the other ends thereof. In this stereo endoscope, the two image guides are paired and incorporated in an insertional part of the endoscope. A convergence angle formed by the pair of objective lenses with respect to an observation object point is set to a value that permits stereo visualization. Thus, the inside of a body cavity can be observed three-dimensionally.

The foregoing conventional stereo endoscope is based on a flexible endoscope. In a rigid stereo endoscope, two relay optical systems are arranged in parallel with each other. Optical images provided by the two relay optical systems are picked up using charge coupled devices (CCDs), thus enabling stereo observation.

U.S. Pat. No. 4,924,853 describes a rigid stereo endoscope that includes two photoconductive means and two shutters, wherein two optical images provided by the photoconductive means are intercepted alternately by the shutters in order to enable stereo observation.

The foregoing rigid stereo endoscope includes, as shown in FIG. 1, a pair of optical systems and a pair of imaging devices (CCDs) 71a and 71b. A pair or objective optical systems 72a and 72b facing a region to be observed are incorporated in the distal part of an insertional part of an endoscope 70. The pair of objective optical systems 72a and 72b are spaced to such an extent that a parallax enabling stereo visualization will be created.

Relay optical systems 73a and 73b for transmitting right and left object images are located behind the objective optical systems 72a and 72b. A shielding plate, which is not shown, is placed between the relay optical systems 73a and 73b.

Angling relay optical systems 74a and 74b which transmit the right and left object images while changing the optical paths are located behind the relay optical systems 73a and 73b. Imagery optical systems 75a and 75b for forming the right and left images are located behind the angling relay optical systems 74a and 74b and in front of the CCDs 71a and 71b.

The right and left object images picked up by the CCDs 71a and 71b are converted into electrical signals. The electrical signals are processed by a signal processing unit 76, and then displayed on a monitor 77.

A procedure for observing a stereo image will now be described. That is to say, right and left images are switched at a high speed and displayed on the monitor. An observer wears special glasses, looks at the left image with his/her left eye and the right image with his/her right eye, and thus has a sense of three-dimensionality.

In recent years, another procedure has been proposed: two small image display elements, such as liquid crystal displays, are employed; a left image is displayed on one of the display elements and a right image is displayed on the other display element; and the right and left images are observed with the right and left eyes, respectively. Thus, three-dimensionality is realized.

In either of the above display procedures, for normal three-dimensionality, the endoscope must be focused at a point of the coincident centers of right and left fields of view (intersection between the optical axes of the right and left optical systems).

In observation using a stereo endoscope, there is a demand for looking at the whole of an object to be observed at a certain distance or observing part thereof in an enlarged scale. To cope with this demand, for example, the conventional endoscope shown in FIG. 1 should be reconstructed in such a manner that zoom optical systems are used as the imagery optical systems 75a and 75b to vary the fields of view.

In the configuration of a conventional stereo endoscope, the right and left optical systems are completely independent of each other. This brings about the following drawbacks:

(1) Minute magnification errors in right and left objective optical systems, relay optical systems, and zoom optical systems are accumulated to appear as a difference in magnification between the right and left optical systems. This becomes outstanding, in particular, when the zoom magnifications are increased.

(2) When the zoom optical systems are used for zooming; that is, when the lenses are moved along the optical axes, movement errors in the right and left zoom optical systems are added to the minute errors described in item (1).

It is difficult to bring the errors mentioned in items (1) and (2) under control. As for the zoom optical systems in a conventional stereo endoscope, the right and left zoom optical systems must be interlocked with each other for fear that the magnifications of right and left images may differ from each other. When increased, the magnifications of right and left images differ from each other more critically. In practice, it is almost impossible to control the foregoing errors. A control mechanism would be very complex.

In addition to a zoom-related drawback, there is a problem concerning focusing. The right and left optical systems must be interlocked with each other and focused simultaneously and correctly. This means that a drawback similar to that concerning the zoom optical systems could occur in the conventional stereo endoscope.

In a stereo endoscope, right and left images having a parallax between them are visualized to provide a sense of three-dimensionality. Since the right and left images have a parallax between them, the contours shown in the images are mismatched a bit. However, as long as the displacements of the display positions of right and left images are within an appropriate range, an observer will observe the right and left images as coincident images and have a sense of three-dimensionality, but do not recognize the images as different images. In short, the observer recognizes the right and left images as one stereo image.

However, when the difference in magnification between right and left images exceeds a limit, the sizes of the images differ from each other. The images therefore do not coincide and are seen as doubled. Thus, an observer fails to recognize the images as a stereo image and fatigue is likely.

When the inconsistency between the centers of right and left fields of view is too great, the displacements of the display positions thereof increase. The right and left images therefore do not coincide with each other and are seen as different images. When right and left images are out of focus or, for example, when one of the right and left images is in focus but the other one is out or focus (blurred), the aforesaid problems occur.

SUMMARY OF THE INVENTION

An object of the present invention is to provide a stereo endoscope and a stereo endoscope imaging apparatus which offer a limited difference in magnification between right and left subject images having a parallax between them, realize optimal three-dimensionality, and tend to reduce fatigue in an observer.

Another object of the present invention is to provide a stereo endoscope that obviates the necessity of interlocking the operations of right and left optical systems, enables easy and uniform adjustment of at least either of magnifications or foci, realizes optimal three-dimensionality, and tends to reduce fatigue in an observer.

Yet another object of the present invention is to provide a stereo endoscope and a stereo endoscope imaging apparatus that attain coincidence between right and left images despite shifts of observation points for right and left object images having a parallax between them, realize optimal three-dimensionality, and tend to reduce fatigue in an observer.

Another object of the present invention is to provide a stereo endoscope which attains coincidence between right and left images despite shifts of observation points for right and left object images having a parallax between them, and allows an observer to see right and left images as an optimal stereo image with his/her naked eyes.

Yet another object of the present invention is to provide a stereo endoscope imaging apparatus which performs electrical processing to attain coincidence between right and left images despite shifts of observation points for right and left subject images having a parallax between them, and displays the right and left images on a monitor while realizing optimal three-dimensionality.

In a preferred working mode of the present invention, a stereo endoscope includes a pair of right and left objective optical systems which are arranged with a predetermined space between them and each of which forms an object image, an image transmitting means for transmitting right and left object images formed by the objective optical systems to desired positions, an imagery optical system which has a single optical axis, receives the right and left object images from the image transmitting means, and forms the right and left object images at predetermined positions, and an imaging means which receives the light carrying the right and left object images formed by the imagery optical system, and converts the received light into electrical signals.

Other features and advantages of the present invention will be fully apparent from the description below.

BRIEF DESCRIPTION OF THE DRAWINGS

FIGS. 2 to 8 relate to the first embodiment of the present invention;

FIG. 2a schematically shows a configuration of a rigid stereo endoscope;

FIG. 2b shows a configuration of a zoom optical system;

FIG. 2c is an explanatory diagram concerning variations of fields of view;

FIG. 2d is an explanatory diagram concerning a shirt in position of coincident observation points;

FIG. 4 is a perspective view showing a specific example of a structure of an imaging device driving means;

FIG. 5 is a perspective view showing a specific example of a structure of an imaging device driving means;

FIG. 6 is a block diagram for explaining the drive and control of a zoom mechanism and a CCD drive mechanism;

FIG. 7 is a block diagram for explaining the drive and control of an optical system/CCD drive mechanism;

FIG. 8 is a block diagram showing circuitry for interlocking a zoom mechanism and a CCD drive mechanism by controlling them in terms of the number of pulses;

FIG. 9a shows a configuration of a stereo endoscope;

FIG. 9b is an explanatory diagram concerning an in-focus position;

FIGS. 1a to 10c relate to the third embodiment;

FIG. 10a shows a configuration of a stereo endoscope;

FIGS. 10b and 10c show another configuration of an objective optical system;

FIG. 11 shows a configuration of a stereo endoscope system;

FIG. 12 is a block diagram showing a circuitry of a signal processing unit;

FIG. 13a shows a configuration of a stereo endoscope;

FIG. 13b shows a configuration of an adjustment optical system capable of focus adjustment and magnification adjustment;

FIG. 13c is an explanatory diagram concerning imaging zones of right and left object images formed on a CCD;

FIG. 14 is a block diagram concerning an example of a circuitry of a signal processing unit;

FIG. 15 shows a configuration of a memory;

FIG. 16 is an explanatory diagram concerning stereo display;

FIGS. 17a and 17b relate to the sixth embodiment;

FIG. 17a schematically shows a configuration of a stereo endoscope; and

FIG. 17b shows configurations of fiber driving means.

DETAILED DESCRIPTION OF THE PREFERRED EMBODIMENTS

Figure 1:
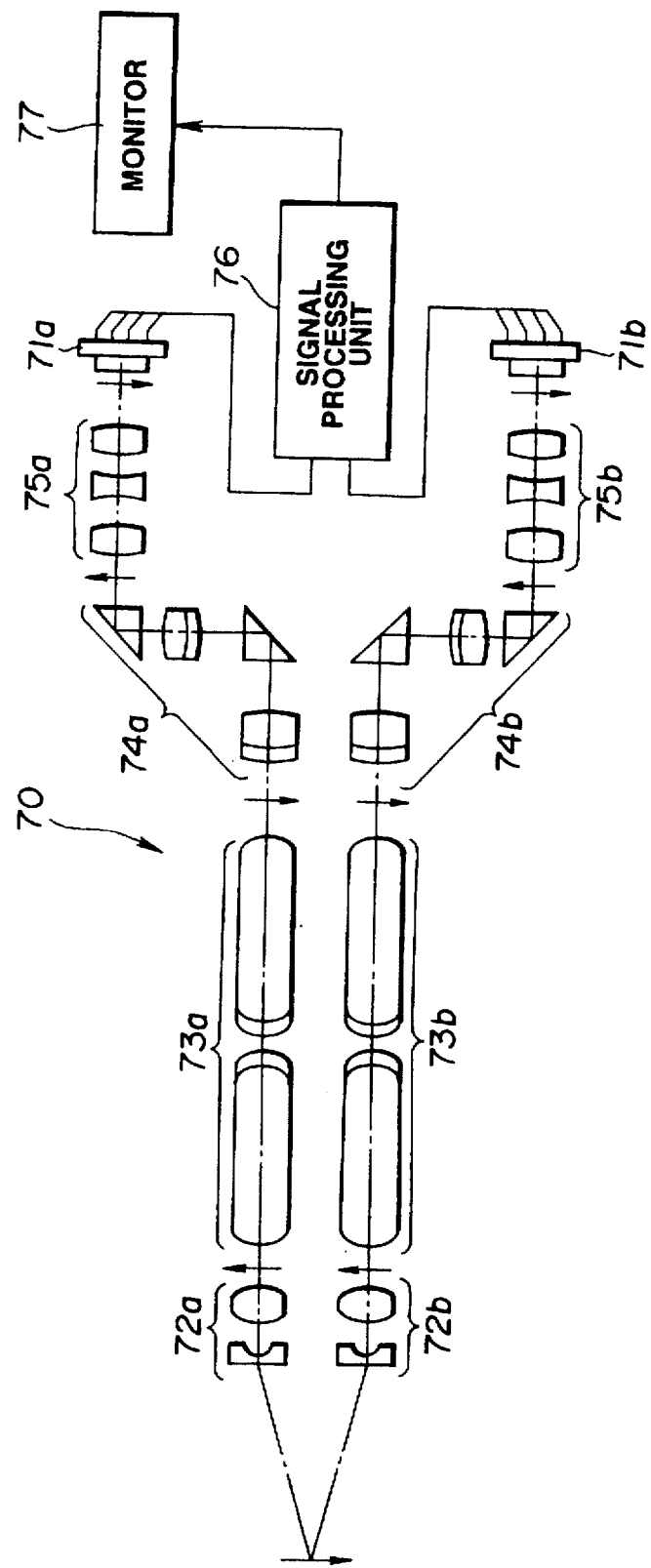
FIG. 1 shows a configuration of a stereo endoscope of the prior art.

FIGS. 2 to 8 relate to the first embodiment of the present invention. FIG. 2a schematically shows a configuration of a stereo endoscope apparatus. FIG. 2b shows a configuration of a zoom optical system. FIG. 2c is an explanatory diagram concerning variations of fields-of-view FIG. 2d is an explanatory diagram concerning a shift of the positions of coincident observation points. FIG. 3 is an explanatory diagram showing variations of fields-of-view and movements of imaging devices.

A stereo endoscope of the present invention will be described using a rigid endoscope as an example.

A stereo rigid endoscope 1 shown in FIG. 2a has a rigid insertional part. The rigid stereo endoscope 1 includes a pair of objective optical systems, a pair of relay optical systems serving as image transmitting means, one imagery optical system, and a pair of solid-state imaging devices, such as CCDs 2a and 2b, serving as imaging means.

A pair of objective optical systems 3a and 3b facing a region to be observed 11 are located in the distal part or the insertional part of the endoscope 1. The pair of objective optical systems 3a and 3b are spaced to such an extent that a parallax permitting stereo visualization will be created.

Relay optical systems 4a and 4b each comprising a plurality of lenses are located behind the objective optical systems 3a and 3b, which transmit right and left object images of the region to be observed 11 backward. The relay optical systems 4a and 4b are formed with equal-power afocal lens systems that transmit incident images toward emission ends without changing the magnifications of the images. A shielding plate (not shown), is placed between the relay optical systems 4a and 4b.

An imagery optical system 5 having one optical axis is located behind the relay optical systems 4a and 4b. The imagery optical system 5 forms the right and left images on the imaging surfaces of the CCDs 2a and 2b.

The right and left object images formed by the CCDs 2a and 2b are converted into electrical signals. The electrical signals are then processed by a signal processing unit (not shown), and displayed on a monitor (not shown). The information derived from the right and left object images is displayed on the monitor alternately on a time-sharing basis, and thus appear as right and left optical images having a parallax between them. An observer wears special glasses and observes the optical images as a stereo image. In the special glasses, the right and left glasses are shielded alternately synchronously with the right and left optical images displayed alternately on a time-sharing basis. Aside from the aforesaid display method, a method of displaying right and left images simultaneously on two monitors is available.

The imagery optical system 5 may be formed with one lens having one optical axis or composed of a plurality of lenses having one optical axis. Unlike an arrangement in which right and left optical systems are employed independently, a difference in magnification hardly occurs. Unlike an arrangement composed of right and left optical systems, the imagery optical system 5 can offer a reduced difference in magnification between right and left object images having a parallax between them.

In this embodiment, the imagery optical system 5 is a variable power optical system; that is, a zoom optical system. A zoom optical system 5A shown in FIG. 2b may be employed. In the zoom optical system 5A shown in FIG. 2b, a lens 12, a variable power lens 13 for changing magnifications, and a compensating lens 14 for compensating for a shift of the location of an image resulting from a magnification change are arranged in that order behind the relay optical systems 4a and 4b. The variable power lens 3 and compensating lens 14 are driven by an optical system driving means 78 and move back and forth along the optical axis, thus changing magnifications.

When the zoom optical system 5A is set to reduce the magnifications of right and left images, the fields-of-view expand as indicated with dashed lines in FIG. 2c. When the magnifications thereof are increased, the fields-of-view shrink as indicated with solid lines in FIG. 2c. When the zoom optical system 5A is set to, for example, expand the fields-of-view (reduce the magnifications), the position of the centers of coincident right and left fields-of-view is, as indicated with dashed lines in FIG. 2d, shifted far behind (point Q1). In other words, the point of the coincident centers (coincident observation points) of the right and left fields-of-view; that is, the intersection between the axes of the right and left optical systems shifts back and forth to points Q1 and Q2 in FIG. 2d.

Figure 3A:
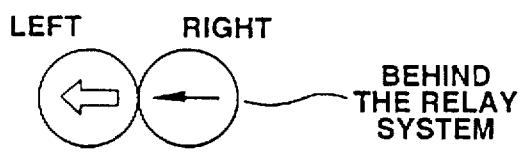
FIGS. 3a to 3g are explanatory diagrams showing variations of fields-of-view and movements of imaging devices.
Figure 3B:
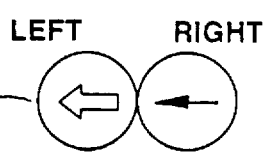
Figure 3C:
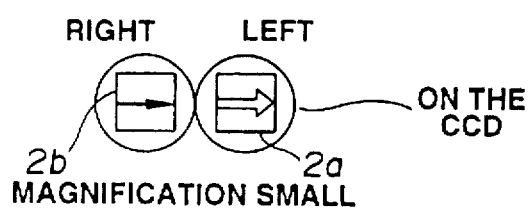

Shifts of imagery positions on CCDs resulting from a shift of the position of coincident centers of fields of view will be described in conjunction with FIG. 3. Right and left images are seen behind the relay optical systems 4a and 4b as shown in FIGS. 3a and 3b irrelevant of the zoom magnifications thereof. Behind the zoom optical system 5A, the positions of the right and left images are mutually switched. When the zooming magnifications are low, as shown in FIG. 3c, the right and left object images are formed within the imaging surfaces of the CCDs 2a and 2b. At this time, as shown in FIG. 3e, the axes of the right and left optical systems intersect at the location of the object 11. In other words, the intersection falls in with the object 11.

Figure 3D:
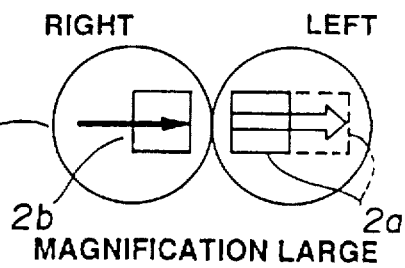
Figure 3E:
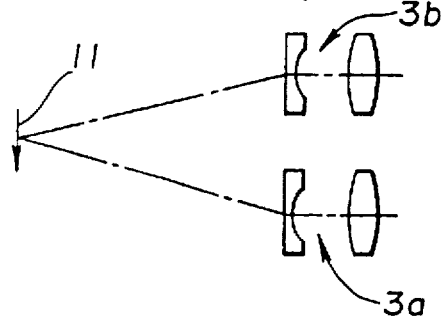

Behind the zoom optical system 5A, when the zooming magnifications are high, as shown in FIG. 3d, the imagery positions get mismatched as the right and left field-of-view expand. Images picked up by the CCDs 2a and 2b differ from each other. Consequently, three-dimenisionality is not realized.

Figure 3F:
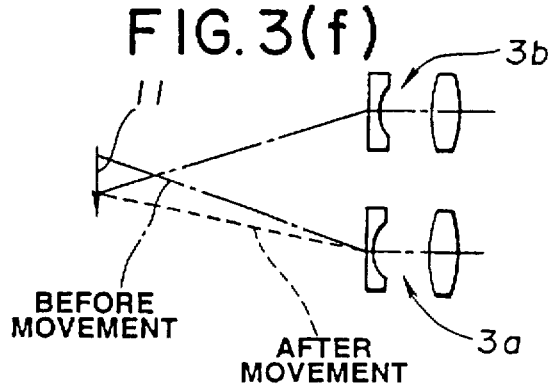

As mentioned above, the position of the coincident centers (coincident observation points) of the right and left field-of-view; that is, the intersection between the axes of the right and left optical systems shifts. In this embodiment, the space between the CCDs 2a and 2b is varied along with zooming. Thus, the position of coincident observation points is held unchanged. In other words, the same position (region to be observed) can be observed all the time with the same three-dimensionality. That is to say, the CCDs 2a and 2b are moved so that the intersection between the axes of the right and left optical systems passing through the centers of the imaging surfaces of the CCDs will intersect at the location of the object 11 as shown in FIG. 3f. In FIG. 3d, as indicated with dashed lines, the CCD 2a is moved so that the left image formed on the CCD 2a will be identical to the right image formed on the CCD 2b. When both the CCDs are moved further with the space between them held intact, an enlarged object image can be observed irrelevant of a region of an object.

Figure 3G:
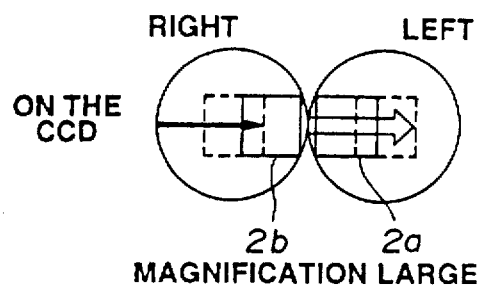

The two CCDs are moved by the same distance in opposite directions indicated with arrows in FIG. 2. With this movement, the intersection between the axes of the right and left optical systems shifts farther away from or closer to the center axis between the objective optical systems 3a and 3b as shown in FIG. 2d. Even after the magnifications of right and left images are varied, the position (region to be observed) that has previously been seen can be seen intact. In other words, even after the zooming magnifications of right and left images are varied, as shown in FIG. 3g, the centers of imaging surfaces of the CCDs 2a and 2b are aligned with the centers of fields of view. A desired region of the object 11 is therefore still imaged. The region that has been positioned previously can be positioned intact in the centers of the imaging surfaces of the CCDs 2a and 2b.

In this embodiment, an arrangement for moving and controlling the CCDs is, as shown in FIG. 2, composed of a movement value detecting means 15, a driving means 16, and a control means 17. The movement value detecting means 15 detects a magnitude of adjusting the zoom optical system 5A for varying the magnifications of right and left images; that is, a magnitude of moving the lenses for varying the magnifications thereof. In general, the lenses constituting a zoom optical system are moved to vary the magnifications of right and left images (which is referred to as magnification adjustment). A magnitude of adjusting the zoom optical system 5A is therefore detected as a magnitude of moving lenses. The driving means 16 changes the space between the CCDs 2a and 2b. In other words, the driving means 16 moves at least either of the CCDs. The control means 17 controls the driving means according to the magnitude of movement detected by the movement value detecting means 15. Under the control of the control means 13, the positions of the CCDs 2a and 2b are varied according to the magnitude of moving lenses.

FIG. 4 is a perspective view showing a specific example of a structure of the driving means 16. The driving means 16 shown in FIG. 4 is a CCD drive mechanism composed of a motor serving as a driving source and gears. In the CCD drive mechanism, two shafts 6 and 7 are running in parallel with the imaging surfaces of the CCDs 2a and 2b, which are located side by side, on the opposite sides of the imaging surfaces. The drive shaft 6 is segmented with a stopper 6a as a center and threaded clockwise and counterclockwise toward both ends to provide male screws 6b and 6c. In the CCDs 2a and 2b, female screws 2c and 2d are threaded to be engaged with the male screws 6b and 6c. The guide shaft 7 is inserted into through holes 2e and 2f of the CCDs 2a and 2b.

A driving gear 10 is fixed to one end of the drive shaft 6 and engaged with a rotary gear 9 of a motor 8 controlled by the control means 17.

In the driving means 16 shown in FIG. 4, the drive shaft 6 rotates with the rotation of the motor 6. At this time, the CCDs 2a and 2b are restrained from rotating by the guide shaft 7. With the rotation of the drive shaft 6, the CCDs 2a and 2b therefore slide along the shafts. Owing to the male screws 6b and 6c threaded on the drive shaft 6 in mutually opposite directions, the CCDs 2a and 2b approach or depart from each other by the same distance.

Figure 5:
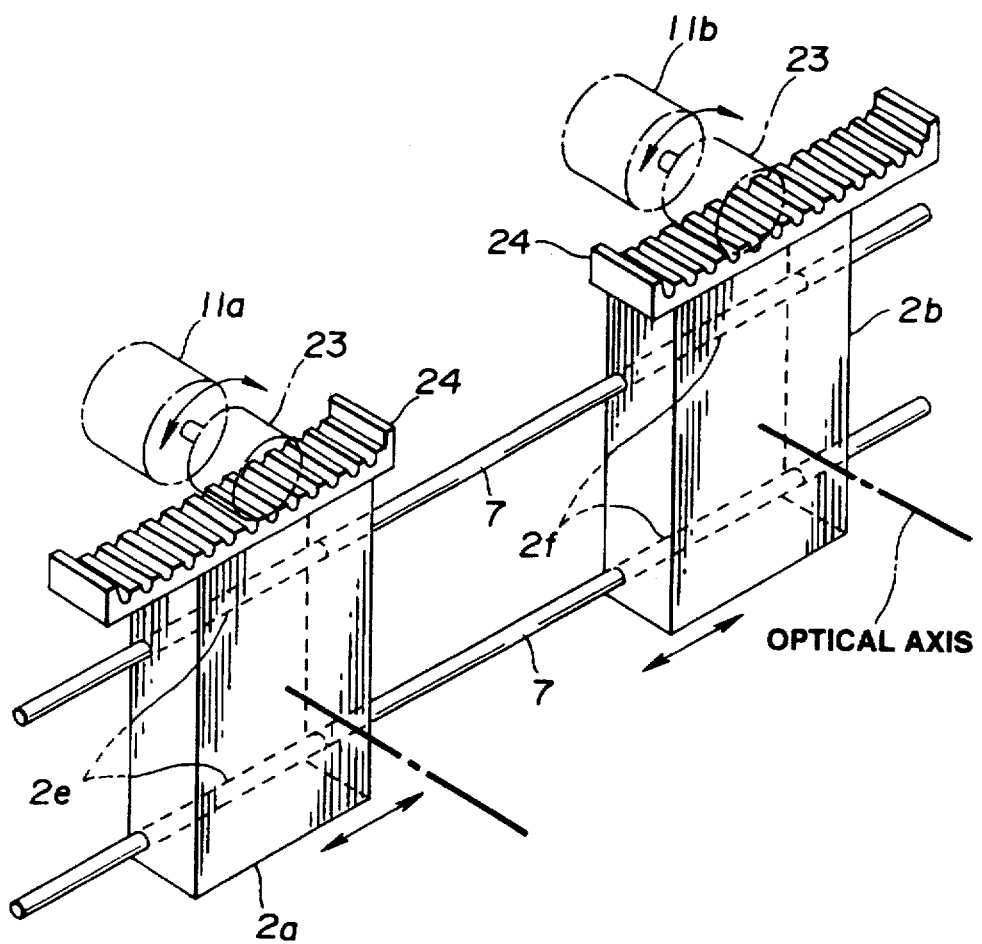

The driving means 16 shown in FIG. 5 includes motors 11a and 11b having gears 23 fixed to rotation axes, racks 24 fixed to the tops of the CCDs 2a and 2b and engaged with the gears 23, and guide shafts 7 inserted in through-holes 2e and 2f similar to those formed in the CCDs 2a and 2b shown in FIG. 4. When the motors 11a and 11b controlled by the control means 17 rotate, the CCDs 2a and 2b having the racks 24 fixed slide along the shafts. The magnitudes and directions of moving the CCDs 2a and 2b correspond to the magnitudes and directions of rotating the motors 11a and 11b.

The foregoing structure allows the CCDs to approach and depart from each other similarly to those in the structure shown in FIG. 4. Furthermore, one of the CCDs can be slided independently.

A zoom mechanism serving as an optical system driving means for moving the variable power lens 13 and compensating lens 14 back and forth along the optical axis can be configured with a known art by combining a motor serving as a driving source, a gear for transmitting a torque of the motor, and a mechanism for converting the torque into a linear reciprocation. Owing to the zoom mechanism, the variable power lens 13 and compensating lens 14 move back and forth along the optical axis with an appropriate space between them. The movement value detecting means 15 may be formed with an encoder that is combined with the motor to detect the magnitude of rotation of the motor. The magnitude of rotation detected by the encoder is regarded as the magnitude of movement of lenses.

In a zoom mechanism of the foregoing known art, a pin projecting from a lens support frame, which is frequently employed for a camera or the like, is fitted in a cam ditch on a cam cylinder, and then the cam cylinder is rotated, while the pin is restrained from rotating. In this mechanism, the movement value detecting means 15 can be composed of, for example, a plurality of conductive patterns formed on the outer circumferential wall of the cam cylinder and a plurality of contacts that contact the conductive patterns. In other words, the movement value detecting means 15 is an encoder. The movement value detecting means 15 is not restricted to the aforesaid example.

Figure 6:
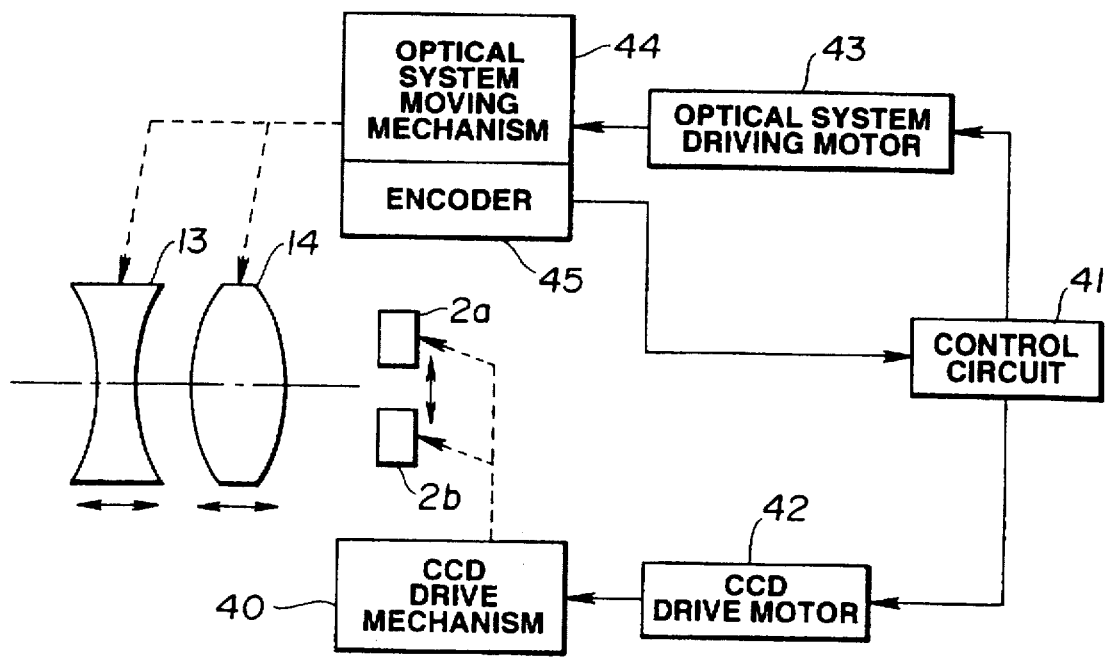

FIG. 6 is a block diagram for explaining the drive and control of a zoom mechanism and a CCD drive mechanism.

A CCD drive mechanism 40 shown In FIG. 6 is driven by a CCD drive motor 42 that is controlled by a control circuit 41 serving as a control means. The CCD drive mechanism 40 thus moves the CCDs 2a and 2b. The CCD drive mechanism 40 is identical to, for example, the CCD drive mechanism shown in FIG. 5. The CCD drive motor 42 corresponds to the motors 11a and 11b. The variable power lens 13 and compensating lens 14 are responsive to the operation of a zoom mechanism 44 serving as an optical system drive mechanism that is driven by an optical system drive motor 43 under the control of the control circuit 41, and moved in parallel with the optical axis. An encoder 45 is formed in, for example, the aforesaid cam cylinder constituting the zoom mechanism 44, and detects the magnitude of movement of the cam cylinder; that is, the magnitude of movement or the lenses 13 and 14. The detected magnitude of movement is fed back to the control circuit 41, and utilized to position the lenses 13 and 14 for zooming and stabilizing the actions of the lenses 13 and 14, and control the magnitude and direction of movement of the CCDs.

Figure 7:
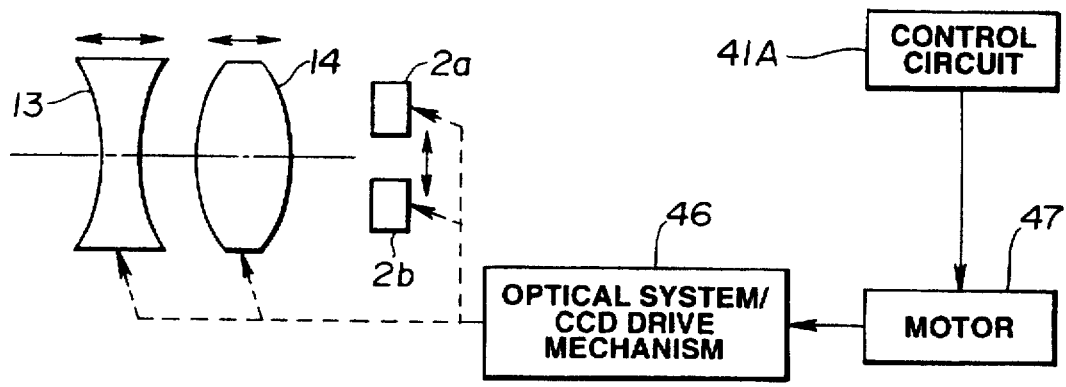

According to a circuitry shown in FIG. 5, a zoom mechanism serving as an optical system drive mechanism and a CCD drive mechanism are mutually interlocked by means of a mechanism composed of gears and others, and one driving source. An optical system/CCD drive mechanism 46 shown in FIG. 7 is composed of a plurality of combinations of gears constituting a zoom mechanism and, for example, gears constituting the CCD drive mechanism shown in FIG. 4. The optical system/CCD drive mechanism 46 thus has a mechanical structure for moving the CCDs 2a and 2b according to the actions of lenses for zooming. The optical system/CCD drive mechanism 46 is driven by a motor 47 that is controlled by a control circuit 41A.

Figure 8:
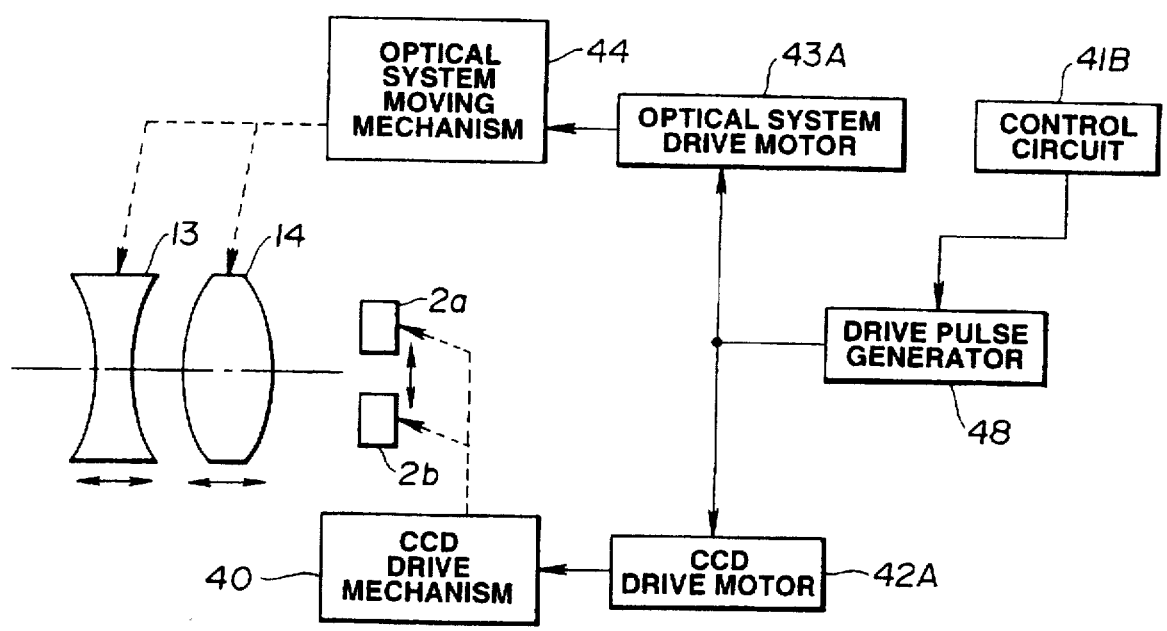

In FIG. 8, two driving sources; that is, pulse motors 42A and 43A are driven at the rate of a predetermined number of pulses per unit time, so that a zoom mechanism and a CCD drive mechanism will be mutually interlocked. A control circuit 41B controls the number of pulses supplied by a drive pulse generator 48 so that the number of pulses to be supplied to the CCD drive motor 42A will have a predetermined relation to the number of pulses to be supplied to the optical system drive motor 43A.

The optical system drive motor 43A drives a zoom optical system using a zoom mechanism 44. The CCD drive motor 42A drives at least either of the CCDs 2a and 2b using a CCD drive mechanism 40. Alternatively, the same number of pulses may be supplied to the motors 42A and 43A, but the gears constituting drive mechanisms may be arranged differently to restrict the magnitude of movement.

In this embodiment, a zoom optical system having a single optical axis is employed. This obviates the necessity of interlocking the operations of right and left optical systems for magnification adjustment. A difference in magnification for zooming between right and left images can be minimized. In this embodiment, a difference in magnification between two object images having a parallax between them can be eliminated. Furthermore, even when the lenses of a zoom optical system are adjusted for zooming, the observation points of right and left fields of view become coincident and the display positions or the right and left images become consistent. An observer therefore experiences an optimal sense of three-dimensionality but feels less fatigued.

Optical fibers may be employed for the relay optical systems 4a and 4b, which results in a flexible insertional part.

Figures 9A, 9B:
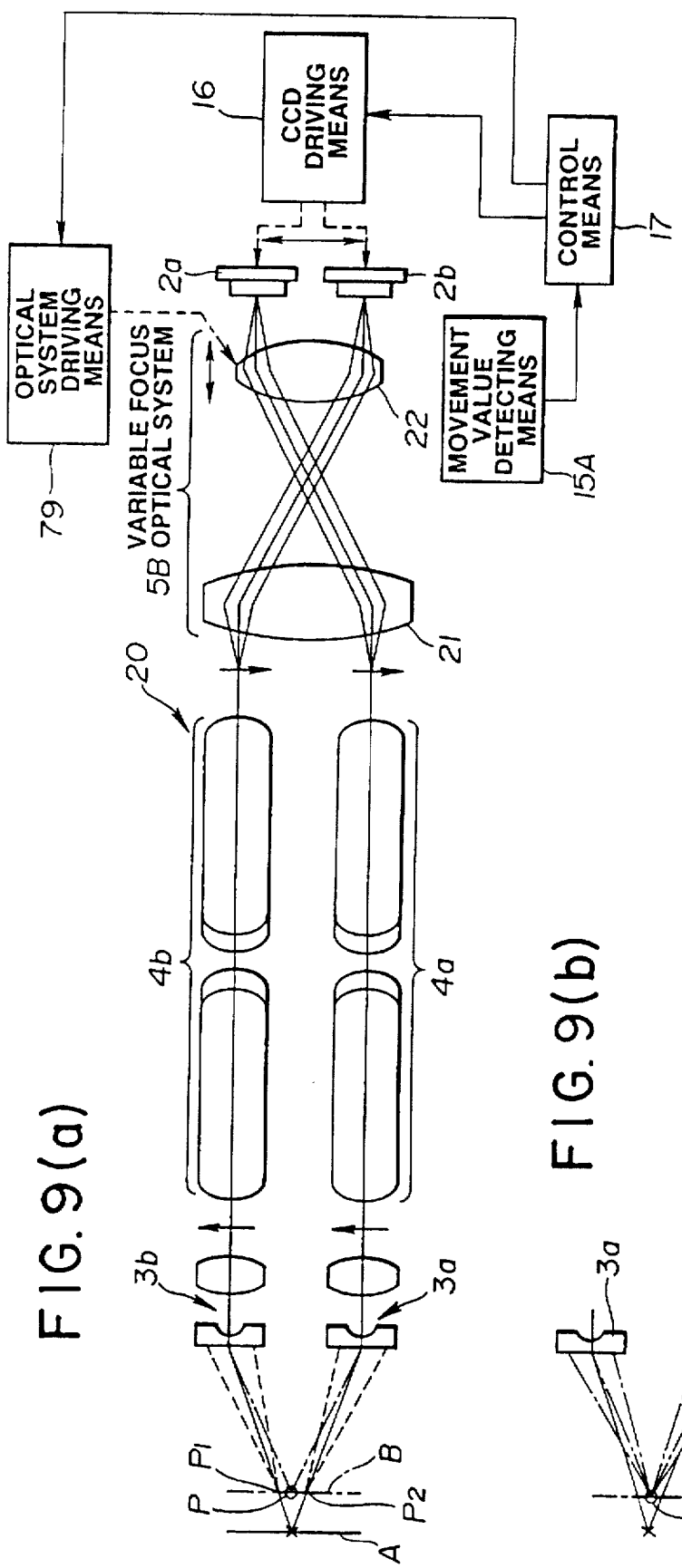
FIGS. 9a and 9b relate to a second embodiment.

FIG. 9a shows a configuration of an endoscope relating to the second embodiment of the present invention. In a stereo endoscope 20 shown in FIG. 9a, the imagery optical system 5 shown in FIG. 2 is designed to perform focusing on behalf of a zoom optical system. That is to say, the stereo endoscope 20 includes a varifocal optical system 5B that is a telecentric optical system having one optical axis. The employment of a telecentric optical system aims to reduce the displacements of the positions of images resulting from focus adjustment. The varifocal optical system 5B has a lens 21 and a focusing lens 22, which is driven by an optical system driving means 79 and moved back and forth along the optical axis for focusing, behind the relay optical systems 4a and 4b. The optical system driving means 79, that is, a mechanism for moving the focusing lens 22; may have the same structure as the zoom mechanism in the first embodiment. A mechanism for driving the CCDs 2a and 2b may have the same structure as the one in the first embodiment. An arrangement for interlocking the operations of the varifocal optical system and CCD mechanism may be identical to any of those shown in FIGS. 6 to 8.

In this embodiment, a movement value detecting means 15A for detecting the magnitude of movement of the focusing lens 22 is installed on behalf or the movement value detecting means 15 shown in FIG. 2. The other components identical to those in the first embodiment are assigned the same reference numerals. No mention will be made of these components and the operation identical to that in the first embodiment.

In the aforesaid configuration, assuming that an object on a plane A indicated with a solid line in FIG. 9a is visualized three-dimensionally, when the foci of the right and left optical systems are adjusted so that an object on a plane B indicated with a dot-dash line in FIG. 9a comes into focus (which is referred to as focus adjustment), unless CCDs are moved, imagery beams follow dashed lines in FIG. 9a. Specifically, the beams reach points P1 and P2 on the plane B at which two solid lines intersect the dot-dash line of the plane B. Images of different positions of an object are therefore formed in the centers of right and left fields-of-view. Although the object on the plane B is in focus, three-dimensionality is not realized.

In the aforesaid configuration, the driving means 16 drives the CCDs 2a and 2b so that the centers of the CCDs will be aligned with the centers of right and left fields or view while being separated from each other by a distance permitting clear observation of right and left images. The optical axes passing through the centers of the right and left fields-of-view intersect at a point P on the plane B as indicated with dot-dash lines in FIG. 9b. This means that the position of an intersection between the right and left optical axes is consistent with an in-focus position. For bringing a near point into focus, the CCDs 2a and 2b are moved toward departing from each other. For bringing a far point into focus, the CCDs 2a and 2b are moved toward approaching mutually. Thus, the space between the right and left CCDs 2a and 2b is varied depending on the detected magnitude of movement of the focusing lens 22.

In this embodiment, a focusing optical system is an optical system having one optical axis. This obviates the necessity of interlocking the operations of right and left optical systems for the purpose of focus adjustment. In this embodiment, two CCDs can be moved so that when an object comes into focus due to focus adjustment, the centers of right and left fields-of-view will be aligned with the centers of display surfaces of the CCDs. This embodiment can therefore provide a clear stereo image and cause an observer to feel less fatigued.

Figures 10A, 10B, 10C:
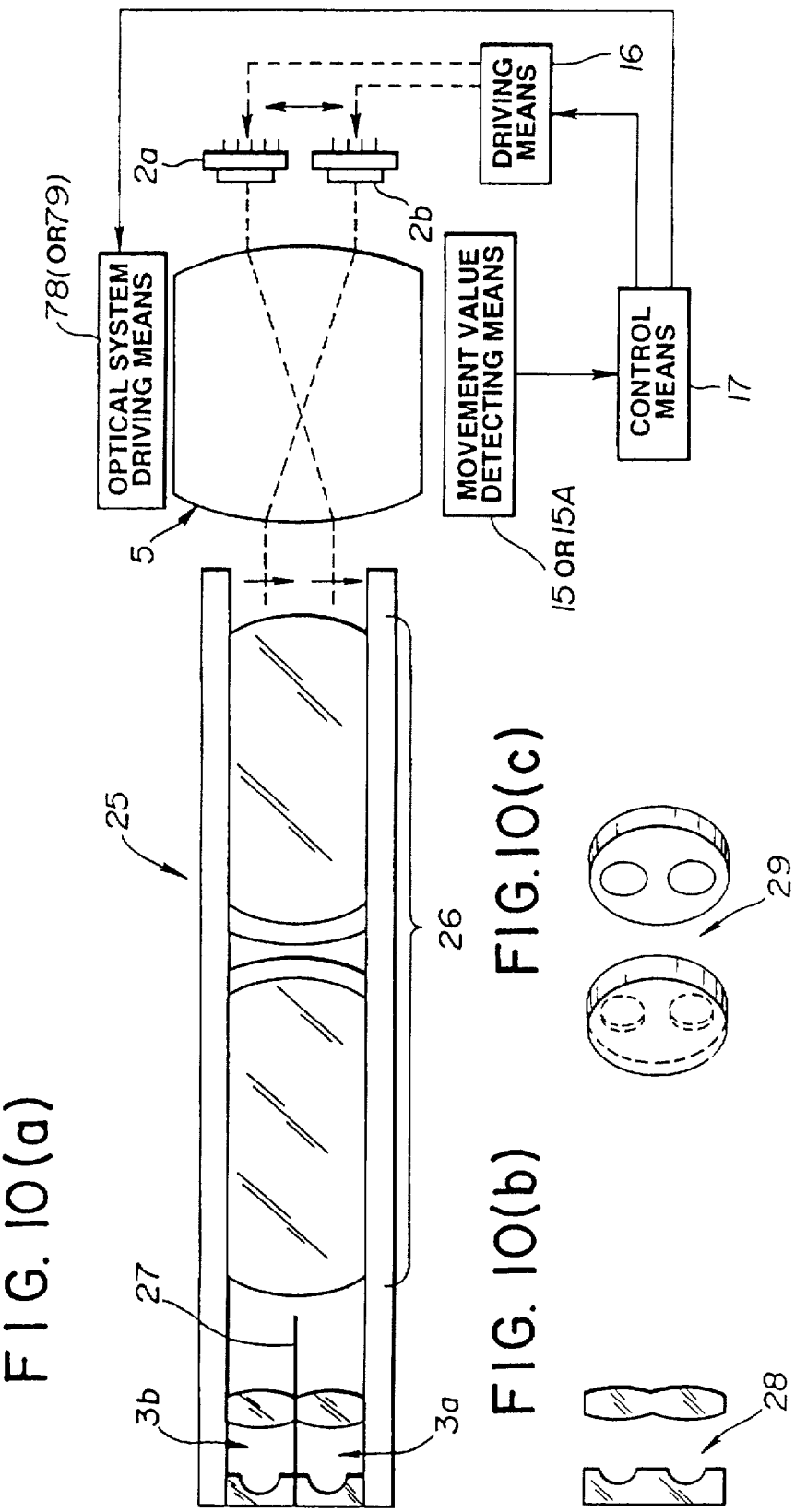

FIG. 10a shows a configuration or a stereo endoscope relating to the third embodiment of the present invention. A stereo endoscope 25 shown in FIG. 10a includes a relay optical system 26, which serves as an image transmitting means having one optical axis, instead of the relay optical systems 4a and 4b shown in FIG. 2. In FIG. 10a, reference numeral 27 denotes a shielding plate for shielding the objective optical systems 3a and 3b for fear that light will enter the objective optical systems. The imagery optical system 5 may be the zoom optical system 5A or varifocal optical system 5B. The other components identical to those in the first or second embodiment are assigned the same reference numerals. No mention will be made of these components and the operation identical to that in the first or second embodiment.

The objective lenses 3a and 3b may he replaced with, as shown in FIG. 10b, an objective lens 28 that is a mold, or as shown in FIG. 10c, an objective optical system 29 that is a lens having the same diameter as the relay optical system 26 and including two portions that possess the capabilities of necessary lenses. Since the objective lens 28 and objective optical system 29 are single units, a difference in magnification between right and left images can be minimized.

The other components and operational effects are identical to those in the first or second embodiment, of which description will therefore be omitted.

FIG. 11 shows a configuration of a stereo endoscope apparatus relating to the fourth embodiment. A stereo endoscope apparatus shown in FIG. 11 comprises a stereo endoscope 20A, a signal processing unit 33, and a monitor 35. The stereo endoscope 20A and signal processing unit 33 constitute a stereo endoscope imaging apparatus. Unlike the aforesaid stereo endoscopes in which two CCDs are moved, in this stereo endoscope imaging apparatus, focus (or zoom) adjustment is achieved by holding CCDs stationary but varying display positions. In the stereo endoscope 20A of this embodiment, the portion starting with the objective lenses 3a and 3b and ending with the CCDs 2a and 2b, and the movement value detecting means 15A and driving means 79 are arranged in the same manner as those shown in FIG. 9a.

In this fourth embodiment, the output signals of the CCDs 2a and 2b are fed to a signal processor 37 in a signal processing unit 33 and subjected to various kinds of signal processing. The processed signals are then fed to an image display timing corrector 34. The image display timing corrector 34 controls the timing of displaying the output signals, which have been subjected to various processing by means of the signal processor 37, so that the output signals will be displayed at appropriate positions on the monitor 35. The image display timing corrector 34 displays the output signals as right and left images at appropriate positions on the monitor 35 according to a magnitude of correction provided by an image shift value generator 36. At this time, the image shift value generator 36 outputs a magnitude of correction; that is, a magnitude of movement of images according to a magnitude of focus adjustment detected by the movement value detecting means 15A.

Figure 12:
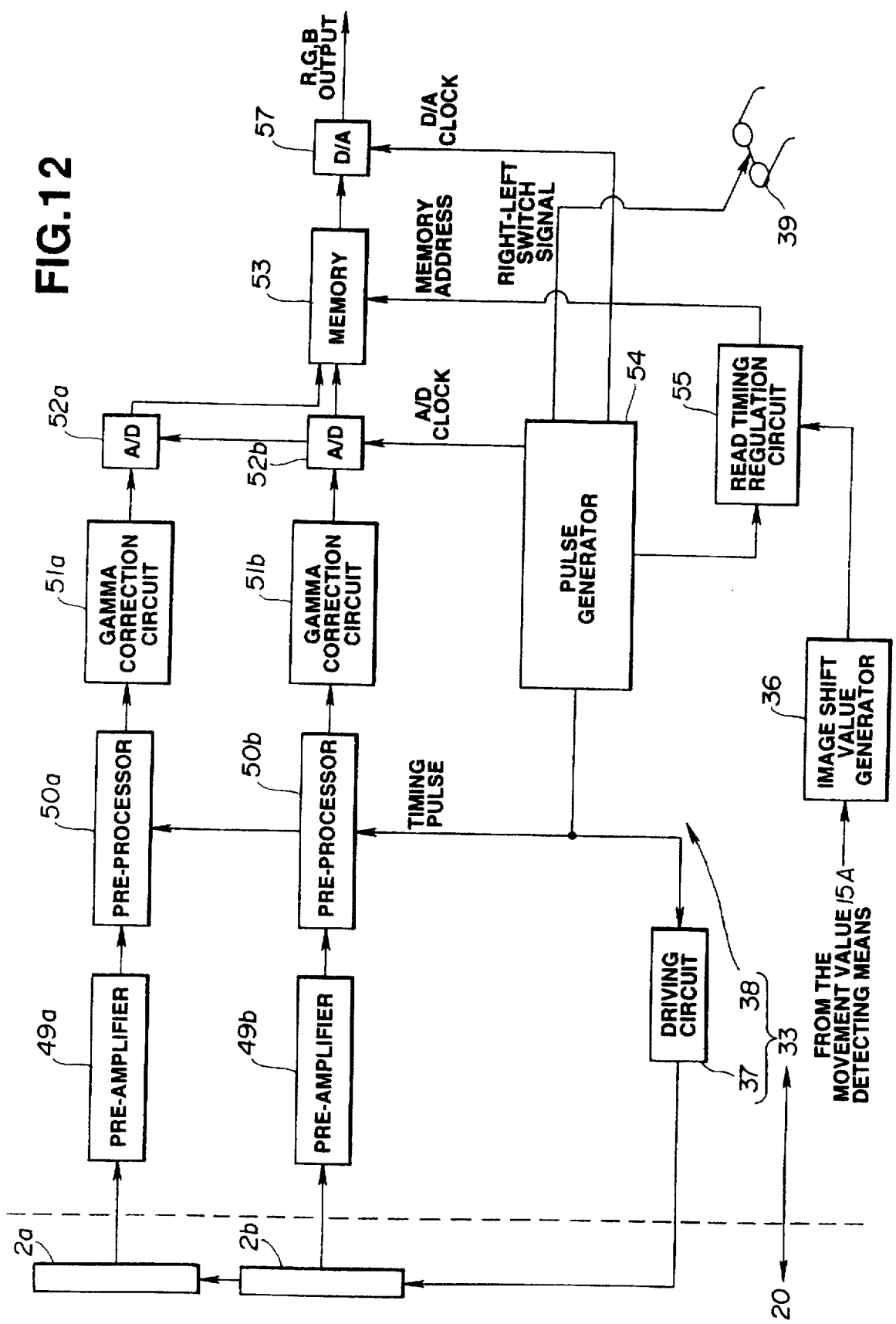

FIG. 12 is a block diagram concerning an example of a circuitry of the signal processing unit 33.

The CCDs 2a and 2b are electrically coupled with a driving circuit 37 and a signal processor 38 incorporated in the signal processing unit.

The objective lenses 3a and 3b are arranged to create a parallax. Optical images having a parallax between them are therefore formed in the imaging areas of the CCDs 2a and 2b. Signals resulting from photoelectric conversion performed by the CCDs 2a and 2b are read with imaging device driving signals applied by the driving circuit 37. The read signals are then fed to the signal processor 38.

The output signals of the CCDs 2a and 2b to be fed to the signal processor 38 are amplified by pre-amplifiers 49a and 49b, and then fed to pre-processors 50a and 50b. The pre-processors 50a and 50b perform various kinds of signal processing such as white balance control, AGC, and iris control.

Output signals of the pre-processors 50a and 50b are fed to gamma correction circuits 51a and 51b, and then subjected to gamma correction. Thereafter, the output signals are converted into digital signals by A/D converters 52a and 52b. The digital signals are temporarily stored in a memory 53.

The signals stored in the memory 53 are read, and then converted into analog signals by a D/A converter 57. The analog signals are then recomposed as standard video signals and supplied to the color motor 35. A pulse generator 54 applies a timing pulse to the driving circuit 37 and preprocessors 50a and 50b.

The pulse generator 54 applies an A/D clock and a D/A clock to the A/D converters 52a and 52b, and the D/A converter 57, respectively. The pulse generator 54 applies a memory address signal and a switch signal to the memory 53. Furthermore, the pulse generator 54 applies a right-left switch signal to liquid crystal glasses 39 synchronously with the display of a right or left image. The memory 53 is one of the components of the image display timing corrector.

In response to a right-left switch signal, when a right image is displayed on the color monitor 35, the right-eye liquid crystal of the liquid crystal glasses 39 becomes transparent and the left-eye liquid crystal thereof becomes interceptive. When a left image is displayed on the color motor 35, the right-eye liquid crystal of the liquid crystal glasses 39 becomes interceptive and the left-eye liquid crystal thereof becomes transparent. Thus, a surgeon observes the right and left images, which are displayed alternately on the color monitor 35, as a stereo image.

The signal processing unit 33 further includes a read timing regulation circuit 55 that is one of the components of the image display timing corrector. The read timing regulation circuit 55 regulates the timing of supplying a memory address signal used to read right and left images stored in a plurality of storage areas in the memory 53. The read timing regulation done by the read timing regulation circuit 55 enables adjustment of display positions of right and left Images on the color monitor 35.

Figures 11A, 11B:
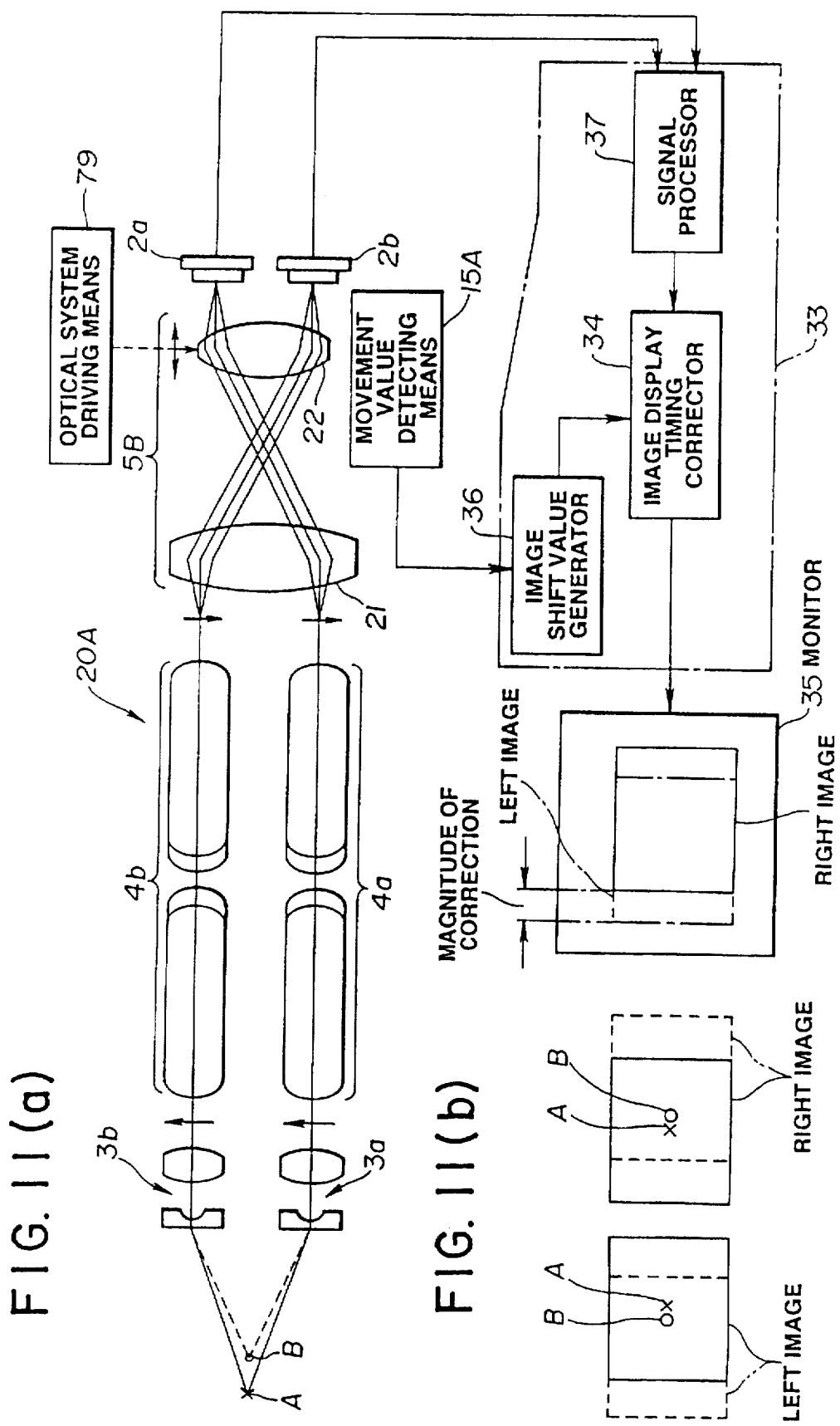
FIGS. 11 and 12 relate to the fourth embodiment.

In the aforesaid configuration, when focus adjustment is performed, a drawback described in conjunction with the second embodiment occurs. Specifically, as shown in FIG. 11b, right and left images are mismatched and displayed at different positions on the monitor 35. The right and left images are therefore not seen as a stereo image.

FIG. 11b shows displacements of the positions of centers of images resulting from focus adjustment.

When the right and left optical systems are to be focused at a point A in FIG. 11a, if the foci thereof are adjusted so that they will focus at a point B, the center positions of right and left images are not aligned with the center of a monitor screen, as shown in FIG. 11b. In this embodiment, the CCDs 2a and 2b are immobilized. The point B in FIG. 11b, which must lie in the centers of the images, is decentered as indicated with dashed lines in FIG. 11b every time focus adjustment is performed. The right and left images must therefore be moved so that the point B will be centered on a monitor screen.

Assuming that a distance from the point A to B is a maximum adjustable length for focus adjustment by the varifocal optical system 5B, a hatched area in FIG. 11b is a common imaging zone. In this embodiment, the common imaging zone, which is shared by the right and left images, is regarded as a display zone of the monitor 35. The timing regulation circuit 55 regulates the timing of applying a memory address signal generated by the pulse generator 54 to the memory 53 and specifies a read location. Thus, the positions of images displayed on the display plane of the color monitor 35 are changed two-dimensionally. Focus adjustment does not cause very large displacements of images. A magnitude of correcting display positions is therefore not very large.

In this embodiment, the image shift value generator 36 provides a magnitude of correction for the read timing regulation circuit 55 according to a magnitude of movement detected by the movement value detecting means 15A. The read timing regulation circuit 55 regulates the timing of reading the memory 53, and corrects the timing of displaying right and left images represented by the signals of the CCDs 2a and 2b. Thus, the display positions of the right and left images are held coincident so that the centers of the right and left images will not be mismatched due to focus adjustment. In this embodiment, the right and left images are displayed with the centers consistent with the centers of the fields-of-view, and coincide with each other. This results in a clear easy-to-see stereo image.

The operational effects are identical to those of the third embodiment, of which description will be omitted. The imagery optical system 5 may be identical to the zoom optical system 5A in the first embodiment.

Figure 13:
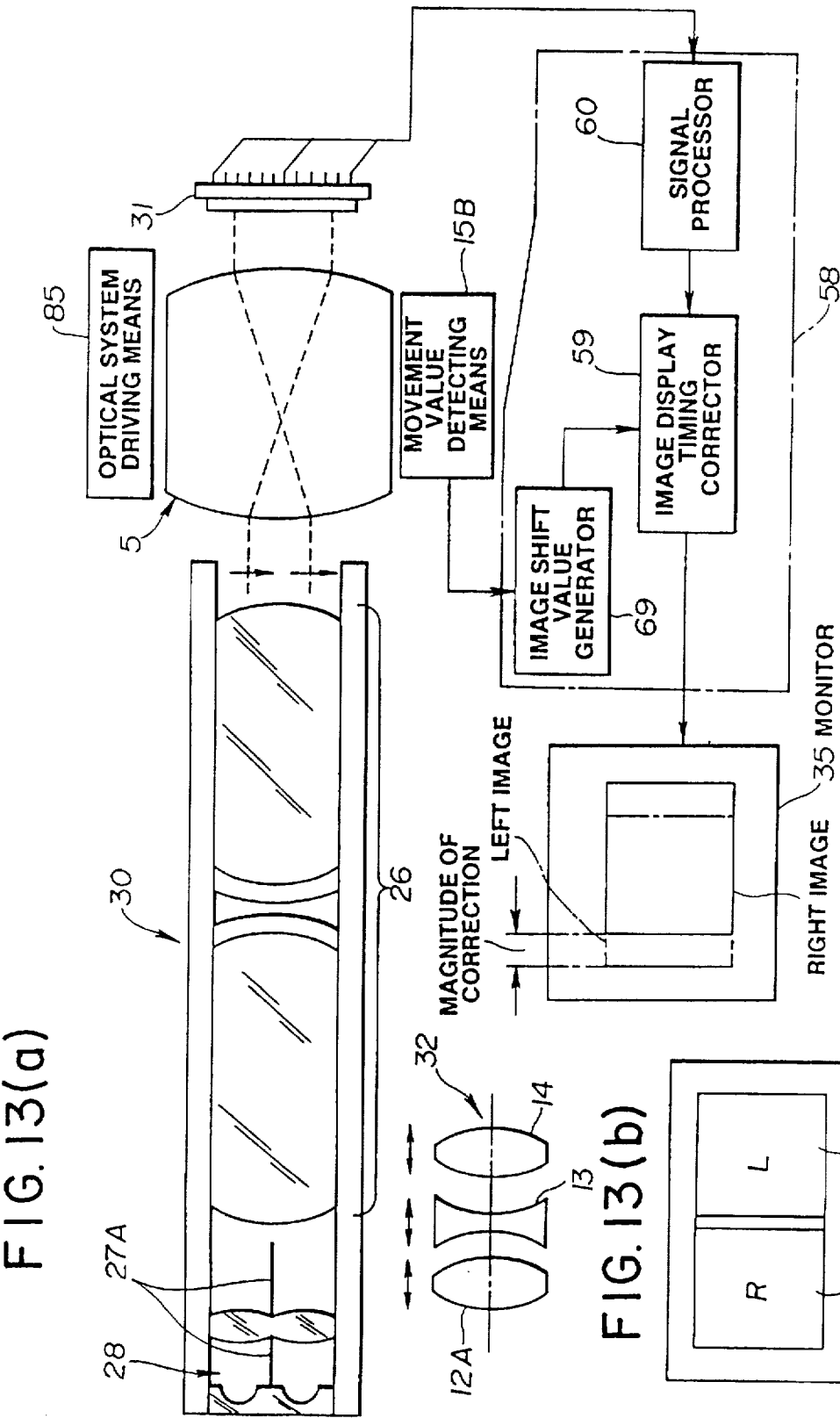
FIGS. 13 to 16 relate to the fifth embodiment.

FIG. 13a shows a configuration of a stereo endoscope apparatus relating to the fifth embodiment of the present invention. A stereo endoscope apparatus shown in FIG. 13a comprises a stereo endoscope 30, a signal processing unit 58, and the monitor 35. The stereo endoscope 30 and signal processing unit 58 constitute a stereo endoscope imaging apparatus.

The stereo endoscope 30 is the same as the endoscope in the third embodiment except that the CCDs 2a and 2b are replaced with a CCD 31. The CCD 31 should preferably be a a high-definition device having a relatively large imaging surface such as a device designed for a high-definition television. The imagery optical system 5 is formed with an optical system 32 capable of adjusting both zooming magnifications and focusing. The optical system 32 is, as shown in FIG. 13b, composed of a focusing lens 12A, a variable power lens 13, and a compensating lens 14 in that order behind a relay optical system 26. The lenses 12A, 13, and 14 are driven by an optical system driving means 85, whereby magnification adjustment and focus adjustment are achieved. The movement value detecting means 15B detects the magnitude of moving the focusing lens 12A, variable power lens 13, and compensating lens 14.

A shielding plate 27A is placed between the right and left lenses of an objective optical system 28.

In this embodiment, as shown in FIG. 13c, right and left images are formed on the same imaging surface of the CCD 31. Electric information resulting from photoelectric conversion are fed to the signal processing unit 58. The imaging surface is segmented into a light-receiving area 31a for a right image and a light-receiving area 31b for a left image. The electric signals are fed to a signal processor 60 in the signal processing unit 58 and then subjected to various kinds of processing. The processed information is then displayed as right and left images on the monitor 35. The signal processing unit 58 has, similarly to that in the fourth embodiment, an image display timing corrector 59 and an image shift value generator 69. The image shift value generator 69 provides a magnitude of correction for the image display timing corrector 59 according to a magnitude detected by the movement detecting means 15B. Components identical to those in the third embodiment are assigned the same reference numerals. No mention will be made of these components and the operation identical to that in the third embodiment.

Figure 14:
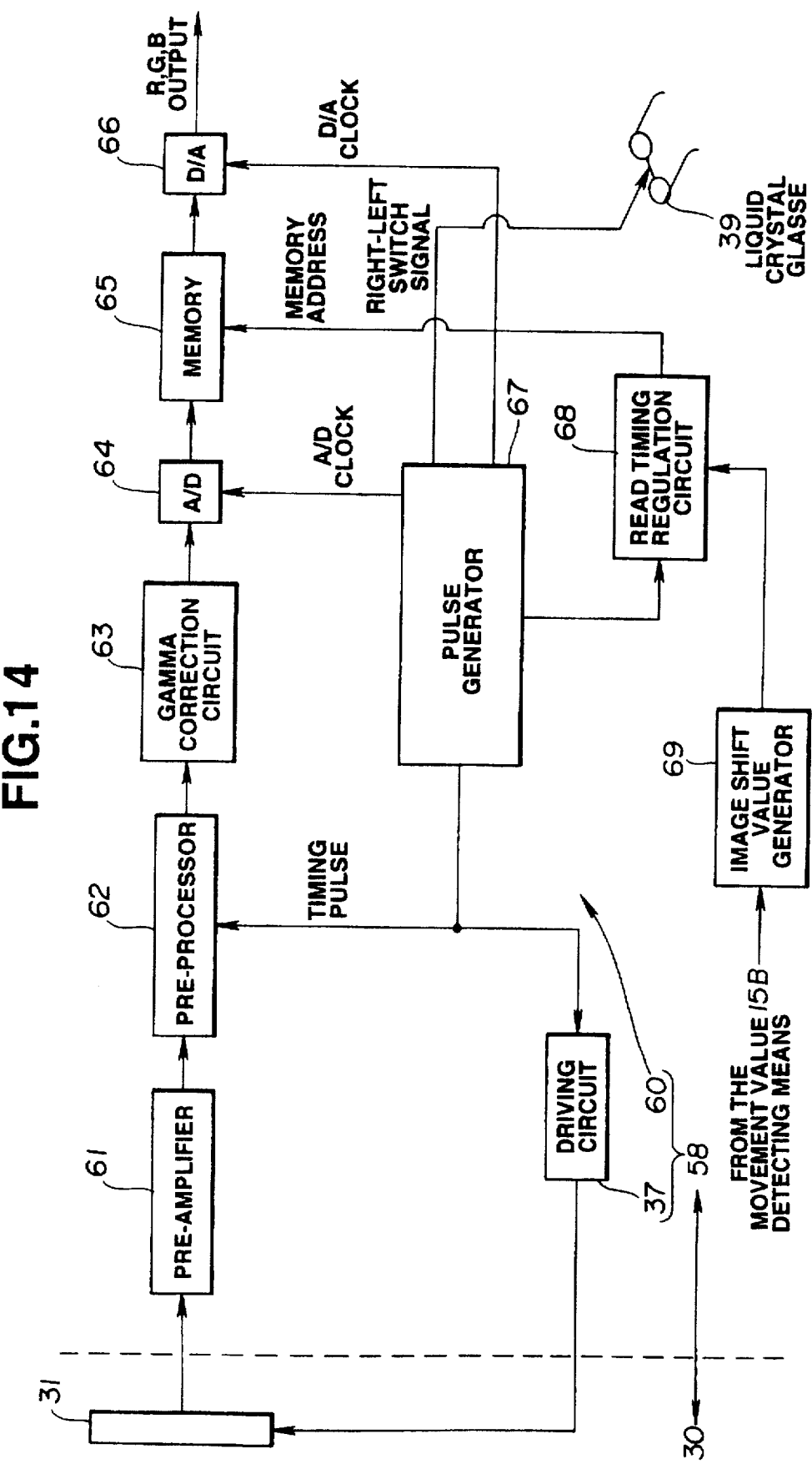

FIG. 14 is a block diagram of circuits for the signal processing unit 58. The signal processing unit 58 includes a pre-amplifier 61, a pre-processor 62, a gamma correction circuit 63, an A/D converter 64, a memory 65, a D/A converter 66, a pulse generator 67, a read timing regulation circuit 68, an image shift value generator 69, and the driving circuit 37. These circuits operate substantially identically to those in the signal processing unit 33 shown in FIG. 12.

Figure 15:
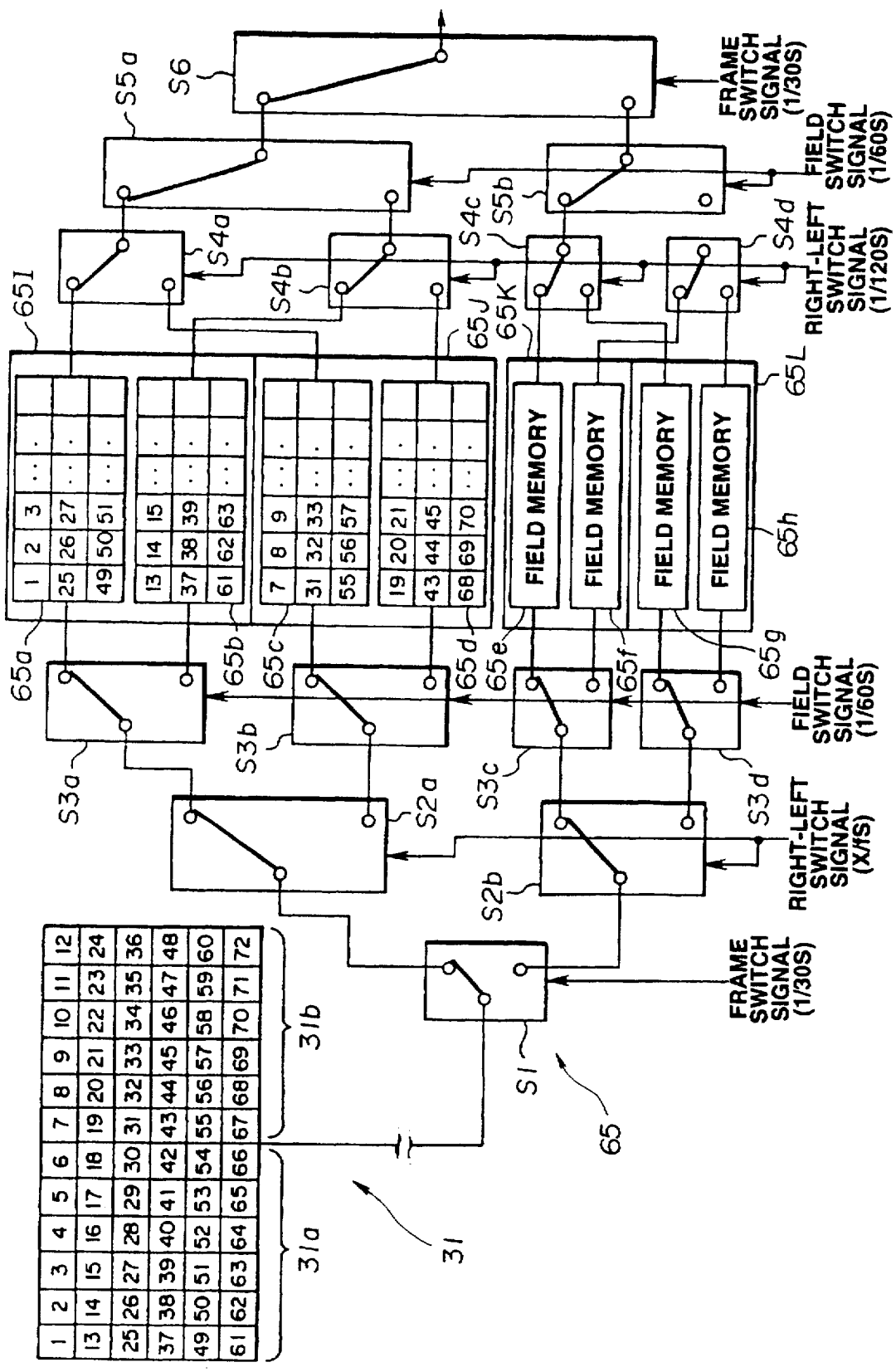
Figure 16:
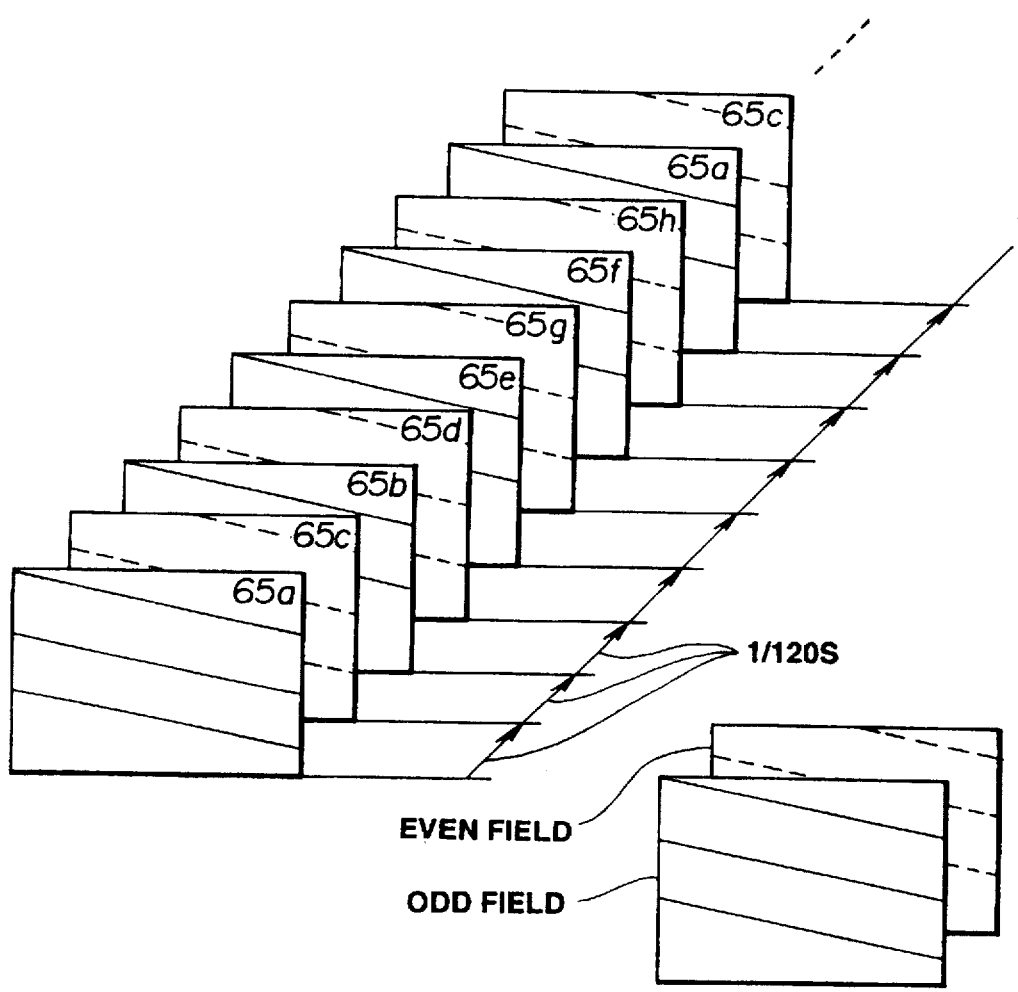

Next, referring to FIG. 15, a configuration of the memory 65 will be described. In this embodiment, an output signal read from the CCD 31 is divided into a right image signal and a left image signal as shown in FIG. 15, and then temporarily stored in the memory 65. Right image signals and left image signals are read alternately frame-by-frame, and then displayed on the color monitor 35 by performing interlaced scanning as shown in FIG. 16.

As shown in FIG. 15, signals representing pixels read from the CCD 31 are temporarily written in eight field memories 65a to 65h via a flame select switch S1, two right-left select switches S2a and S2b, and four field select switches S3a to S3d.

The signals written in the field memories 65a to 65h are read after passing through four right-left select switches S4a to S4d, two field select switches S5a and S5b, and a frame select switch S6. The read signals are fed as output signals of the memory 65 to the D/A converter 37 in the next stage, and then converted into analog signals.

The frame select switches S1 to S6 are switched with a frame switch signal having a duration of one-thirtieth of a second. The field select switches S3a to S3d, S5a, and S5b are switched with a field switch signal having a duration of one-sixtieth of a second. The right-left select switches S4a to S4d are switched with a right-left switch signal having a duration of 1/120 sec.

Assuming that the number of horizontal pixels for a right or left image is X and a horizontal transfer clock frequency is f (Hz), the right-left select switch S2a or S2b is switched at intervals of a product of X by fS.

Adjoining two field memories of the field memories 65a to 65h; that is, field memories 65a and 65b, 65c and 65d, 65e and 65f, and 65g and 65h, are paired to form four frame memories; that is, a right image frame memory 65I, a left image frame memory 65J, a right image frame memory 65K, and a left image frame memory 65L.

As seen from FIG. 14, signals for one frame read from, for example, the light-receiving area 31a for a right image are stored in the two field memories 65a and 65b, which constitute the right image frame memory 65I, in an interlaced manner. Likewise, signals for one frame read from the light-receiving area 31b for a left image are stored in the two field memories 65c and 65d, which constitute the light image frame memory 65J, in an interlaced manner.

The field memories 65a to 65h are, as shown in FIG. 16, read in the order of the field memories 65a, 65c, 65b, 65d, 65e, 65g, 65h, 65a, 65c, etc. Thus, right and left images are displayed alternately on the monitor 35 by performing interlaced scanning.

For example, when the intersection between the optical axes of right and left optical systems appears in right and left images displayed alternately on the monitor 35, if the intersection is displayed at inconsistent positions in the right and left images, the read timing should merely be regulated. Thus, similarly to the first embodiment, the intersection can be displayed at consistent positions in the right and left images without moving the CCD.

As for the display of the intersection, it is also possible to display the intersection in a rightward side of a right image and in a leftward side of a left image.

In FIG. 16, solid lines indicate even fields and dashed lines indicate odd fields. In this embodiment, an image for one frame processed by the CCD 31 is displayed for one-thirtieth of a second. In other words, each of right and left frame images is displayed for one-sixtieth of a second.

In this embodiment, similarly to the aforesaid embodiments, right and left images are displayed on a monitor for stereo visualization. When magnification adjustment or focus adjustment is performed, a movement value detecting means detects a magnitude of moving lenses for the adjustment. Signals representing right and left images of a divided image are fed to, for example, the image display timing corrector 59 shown in FIG. 13, whereby the display positions of the right and left images are changed.

FIG. 17a schematically shows a configuration of a stereo endoscope relating to the sixth embodiment.

A stereo endoscope 80 in this embodiment differs from those in the aforesaid embodiments in a point that right and left images are not displayed on a monitor but observed directly with naked eyes through an eyepiece unit. Components identical to those In the first embodiment are assigned the same reference numerals. No mention will be made of these components and the operation identical to that in the first embodiment. The difference alone will be described.

The stereo endoscope 80 has image guide fibers 81a and 81b (hereinafter, image guides) and eyepieces 82a and 82b, which constitute an eyepiece optical system, instead of the CCDs 2a and 2b in the first embodiment. Right and left object images formed by the imagery optical system 5 are transmitted toward naked eyes by means of the image guides 81a and 81b, and formed at the positions on the CCDs observed with the naked eyes 83a and 83b via the eyepieces 82a and 82b.

The image guides 81a and 81b have flexibility. A fiber driving means 84 varies the space between the image guides. The fiber driving means 84 moves the ends of the image guides 81a and 81b by the side of the imagery optical system 5, which can be composed of the drive mechanism and driving source shown in FIG. 4 or 5.

FIG. 17b shows another structure of the fiber driving means 84. In the fiber driving means 84, driving bars 87a and 87b projecting from the tips of piezoelectric elements 86a and 86b are abutted against the walls of the ends of the image guides 81a and 81b by the side of the imagery optical system 5. A control means 17 applies a driving signal to the piezoelectric elements 86a and 86b. The ends of the image guides 81a and 81b by the side of the imagery optical system 5 move laterally by a distance corresponding to the electrical size or the applied driving signal. The structure shown in FIG. 17b may apply to the CCD driving means 16 in the previous embodiments.

In this embodiment, even when zooming magnifications or foci are adjusted, since the ends of the image guides 81a and 81b by the side of the imagery optical system 5 are moved, an optimal stereo image can always be observed with the naked eye. This embodiment causes an observer to feel less fatigued.

In the aforesaid embodiments, the optical system shown in FIG. 13b may be employed as the imagery optical system.

In the present invention, it will be apparent that a wide range of different working modes can be realized on the basis of the spirit of the invention. This invention will not be limited to the appended claims but not restricted to any specific working modes.

What is claimed is:

1. A stereo endoscope imaging apparatus comprising:

a pair of right and left objective optical systems opposed to an object and arranged with a predetermined space therebetween so as to form a right object image and a left object image, respectively;

an image transmitting means for transmitting said right object image and said left object image formed to predetermined positions by said objective optical systems;

an imagery optical system having a single optical axis, for receiving said right and left object images from said image transmitting means and forming said right and left object images at predetermined positions; and an imaging means for receiving said right and left object images from said imagery optical system and converting them into electrical signals, wherein said imaging means includes two imaging devices that are arranged to optically receive said right and left object images formed by said imagery optical system, and which convert said right and left object images into electrical signals, wherein said imagery optical system includes an adjustment optical system for performing at least one of magnification adjustment and focus adjustment on said right and left object images transmitted by said image transmitting means, said stereo endoscope imaging apparatus comprising:

a driving signal supplying means for applying a driving signal for reading electrical signals resulting from photoelectric conversion performed by said two imaging devices;

an optical system driving means for driving said adjustment optical system to effect at least one of said magnification adjustment and said focus adjustment;

a detecting means for detecting magnitude of adjustment effected by said adjustment optical system driven by said optical system driving means;

an image display timing correcting means for correcting the timing of displaying electrical signals, which is read by said driving signal supplying means and displayed as right and left images in a display means, so as to change at least one of the display positions of said right and left images; and an image shift value generating means for providing a magnitude of correction of the display timing effected by said image display timing correcting means according to the magnitude of adjustment detected by said detecting means, wherein said image display timing correction means includes:

a memory means for temporarily storing electrical signals read with said driving signal; and a read timing regulating means for regulating the timing of reading electrical signals as right and left images from said memory means according to a magnitude of correction effected by said image shift value generating means.

* * * * *